(12) United States Patent
Jameel

(10) Patent No.: US 12,154,689 B2
(45) Date of Patent: *Nov. 26, 2024

(54) METHOD, APPARATUS, AND COMPUTER READABLE MEDIA FOR ARTIFICIAL INTELLIGENCE-BASED TREATMENT GUIDANCE FOR THE NEUROLOGICALLY IMPAIRED PATIENT WHO MAY NEED NEUROSURGERY

(71) Applicant: Mohamed Anver Jameel, Irving, TX (US)

(72) Inventor: Mohamed Anver Jameel, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/956,474

(22) Filed: Sep. 29, 2022

(65) Prior Publication Data
US 2023/0026688 A1    Jan. 26, 2023

Related U.S. Application Data

(63) Continuation of application No. 16/408,709, filed on May 10, 2019, now Pat. No. 11,495,353.

(Continued)

(51) Int. Cl.
*G16H 50/20* (2018.01)
*G16H 10/40* (2018.01)
(Continued)

(52) U.S. Cl.
CPC .............. *G16H 50/20* (2018.01); *G16H 10/60* (2018.01); *G16H 70/20* (2018.01); *G06N 3/02* (2013.01);
(Continued)

(58) Field of Classification Search
CPC ........ G16H 10/00–80/00; G16H 50/20; G16H 10/40; G16H 10/60; G16H 30/40;
(Continued)

(56) References Cited

U.S. PATENT DOCUMENTS 9,286,440 B1 *   3/2016   Carter ................... G16H 40/63
10,346,979 B2    7/2019   Mansi et al.
(Continued)

FOREIGN PATENT DOCUMENTS

EP         3900625 A1      10/2021
WO    WO-2014197669 A1 *  12/2014    ........... G06F 40/143

OTHER PUBLICATIONS

Murthy V. Devarakonda et al., Automated problem list generation and physicians perspective from a pilot study, 105 International Journal of Medical Informatics , 121-129 (2017), https://www.sciencedirect.com/science/article/pii/S1386505617301648 (last visited May 24, 2024) (Year: 2017).*

(Continued)

*Primary Examiner* — Jonathon A. Szumny
*Assistant Examiner* — Nicholas Akogyeram, II
(74) *Attorney, Agent, or Firm* — KATTEN MUCHIN ROSENMAN LLP

(57) ABSTRACT

Method, apparatus, and computer-readable media providing medical personnel artificial intelligence (AI)-derived data regarding a patient presenting neurological indications includes a guidance server. Preferably, the guidance server receives three or more of: (i) natural language input from medical personnel, (ii) real-time vital signs telemetry data, (iii) neurosurgical treatment database information, (iv) neurosurgical treatment guideline information, (v) clinical laboratory testing results, (vi) patient historical data, and (vii) patient imaging information. An imaging post-processor receives (i) patient imaging history information, (ii) and
(Continued)

real-time patient imaging data, and provides to the guidance server the patient imaging information. The guidance server then provides one or more alerts (or other guidance) to the medical personnel.

24 Claims, 6 Drawing Sheets

Related U.S. Application Data

(60) Provisional application No. 62/669,600, filed on May 10, 2018.

(51) Int. Cl.
  G16H 10/60      (2018.01)
  G16H 30/40      (2018.01)
  G16H 70/20      (2018.01)
  G06N 3/02           (2006.01)
  G16H 20/70          (2018.01)

(52) U.S. Cl.
  CPC ............. *G16H 10/40* (2018.01); *G16H 20/70* (2018.01); *G16H 30/40* (2018.01)

(58) Field of Classification Search
  CPC ....... G16H 70/20; G06F 1/00–2221/00; G06Q 10/00–2250/00
  USPC .......................................................... 705/2
  See application file for complete search history.

(56) References Cited

U.S. PATENT DOCUMENTS

| | | | |
|---|---|---|---|
| 10,373,315 B2 | 8/2019 | Mansi et al. | |
| 10,614,572 B2 | 4/2020 | Mansi et al. | |
| 10,733,730 B2 | 8/2020 | Mansi et al. | |
| 11,151,407 B2 | 10/2021 | Walach et al. | |
| 11,328,400 B2 | 5/2022 | Levi et al. | |
| 2010/0312139 A1* | 12/2010 | Dash .................. | G01N 33/6893 435/7.8 |
| 2013/0231947 A1* | 9/2013 | Shusterman ........... | G16H 40/67 705/2 |
| 2015/0025329 A1 | 1/2015 | Amarasingham et al. | |
| 2015/0161331 A1* | 6/2015 | Oleynik ................. | G16H 20/00 705/3 |
| 2015/0294089 A1* | 10/2015 | Nichols ................... | G06F 3/167 705/3 |
| 2017/0098195 A1* | 4/2017 | Douglas ............. | G06Q 10/1093 |
| 2018/0090231 A1 | 3/2018 | Liederman et al. | |
| 2019/0150857 A1* | 5/2019 | Nye ....................... | G16H 30/40 |
| 2020/0043612 A1* | 2/2020 | McNair .................. | G16H 50/30 |
| 2020/0167881 A1 | 5/2020 | Sheffer et al. | |
| 2020/0411173 A1 | 12/2020 | Mansi et al. | |
| 2021/0057112 A1 | 2/2021 | Mansi et al. | |
| 2021/0065358 A1 | 3/2021 | Walach et al. | |
| 2022/0230288 A1 | 7/2022 | Levi et al. | |
| 2022/0261985 A1 | 8/2022 | Walach et al. | |
| 2022/0343142 A1 | 10/2022 | Jimenez Pastor et al. | |

OTHER PUBLICATIONS

Thomas J. Esposito, et al., "Neurosurgical Coverage. Essential, Desired, or Irrelevant for Good Patient Care and Trauma Center Status", Annals of Surgery, Sep. 2005, 242(3): 364-374.

Jeffrey L. Saver, "Time is brain/spinal cord" in the Article "Time is Brain-Quantified", Stroke, 2006, 37: 263-266, available at http://stroke.ahajournals.org/content/37/1/263.

Margaret Rouse, "Clinical Document Architecture (CDA)", available at https://searchhealthit.techtarget.com/definition/Clinical-Document-Architecture-CDA, 2 sheets.

Michele Larobina, et al., "Medical Image File Formats", Journal of Digital Imaging, Apr. 2014, 27(2), 200-206, DOI 10.1007/s10278-013-9657-9.

Karl Freund, "Will ASIC Chips Become the Next Big Thing in AI?", Forbes Magazine, Aug. 4, 2017, 8 sheets, available at https://www.forbes.com/sites/moorinsights/201 7 /08/04/will-asic-chips-become-the-next-big-thing-in-ai/?sh=5d20ced911d9.

Nancy Carney, et al., "Guidelines for the Management of Severe Traumatic Brain Injury 4th Edition", Sep. 2016, pp. 1-244, available at https://braintrauma.org/uploads/13/06/ Guidelines_for_Management_of_Severe_TBI_4th_Edition.pdf.

William J. Powers, et al., "2018 Guidelines for the Early Management of Patients With Acute Ischemic Stroke: A Guideline for Healthcare Professionals From the American Heart Association (AHA)/American Stroke Association (ASA)", Jan. 24, 2018, pp. e46-e99, DOI: 10.1161/STR.0000000000000158.

"Direct to CT/MRI Protocols", Oct. 2014, 2 sheets, available at https://www.heart.org/-/media/files/professional/quality-improvement/target-stroke/target-stroke-phase-ii/ts_directtoct_ucm_ 470723.pdf?la=en.

"Patient Time Tracker", 2014, 1 sheet, available at https://www.heart.org/-/media/files/professional/quality-improvement/target-stroke/ta rget-stroke-phase-iii/9-17 -u pdate/exhibit-e2--gwtg-ts-timetracker_ word-v2.pdf?la =en.

"New Brain Metastases Treatment Guidelines", Published in the Journal of Neuro-Oncology, Dec. 2, 2009, 7 sheets, aval 1 able at https://www. a ans. org/pdf/Legislative/Brai n MetastasesGu idel i nesSu mmary1209. pdf.

Senders J.T. et al. Natural and artificial intelligence in neurosurgery: a systemic review. Neurosurgery. 2017; 0; 1-12. Published Sep. 7, 2017.

Notice of Allowance dated Jun. 30, 2022, from U.S. Appl. No. 16/408,709, 35 sheets.

Non-Final Rejection dated Mar. 2, 2022, from U.S. Appl. No. 16/408,709, 63 sheets.

Final Rejection dated Sep. 30, 2021, from U.S. Appl. No. 16/408,709, 44 sheets.

Non-Final Rejection dated Mar. 18, 2021, from U.S. Appl. No. 16/408,709, 36 sheets.

International Search Report and Written Opinion mailed Aug. 21, 2019, from International Application No. PCT/US2019/031711, 17 sheets.

Notice of Allowance dated Apr. 18, 2024, from U.S. Appl. No. 18/411,519, 29 sheets.

Communication pursuant to Article 94(3) EPC dated Dec. 11, 2023, from European Patent Application No. 19737928.2, 8 sheets.

Non-Final Rejection dated Mar. 28, 2024, from U.S. Appl. No. 18/411,519, 47 sheets.

Murthy V. Devarakonda et al., Automated problem list generation and physicians perspective from a pilot study, 105 International Journal of Medical Informatics, 121-129 (2017), https://www.sciencedirect.com/science/article/pii/S1386505617301648 (last visited Mar. 21, 2024) (Year: 2017).

\* cited by examiner

METHOD, APPARATUS, AND COMPUTER READABLE MEDIA FOR ARTIFICIAL INTELLIGENCE-BASED TREATMENT GUIDANCE FOR THE NEUROLOGICALLY IMPAIRED PATIENT WHO MAY NEED NEUROSURGERY

CROSS REFERENCE TO RELATED APPLICATIONS

This application is a continuation application of U.S. patent application Ser. No. 16/408,709, filed May 10, 2019, which claims priority of U.S. Provisional Application Ser. No. 62/669,600, filed May 10, 2018, the contents of which are incorporated herein by reference.

BACKGROUND OF THE INVENTION

The present invention generally relates to utilizing artificial intelligence to assist Doctors and other care-givers to quickly assess and determine care-protocols for patients who may have neurological impairments (often while presenting with other physical impairments).

There were 5273 Emergency Rooms (ERs) in the US in 2015, over 5700 hospitals, and less than 3700 neurosurgeon covering a US population of 326 million. To serve this population, the U.S. has only approximately 3,500-4,000 neurosurgeons. Of course, the number of neurosurgeons immediately available to any of these ERs for an emergency consultation is much smaller at any one point in the day at any given location. See, for example, the article entitled: "Neurosurgical Coverage. Essential, Desired, or Irrelevant for Good Patient Care and Trauma Center Status", Thomas J. Esposito, et al., ANNALS OF SURGURY, September 2005, 242(3): 364-374. Note the teaching in the Summary: "The availability of neurosurgeons for trauma patients is increasingly sparse" The 213,000 or so reported head injuries form only a portion of the emergencies requiring a neurosurgical consultation or intervention. Presentations of other neurological impairments requiring an emergent neurosurgical consultation or intervention abound; decompensating tumors, hemorrhagic and large ischemic stroke, post-operative decompensation, and others.

See also the phrase "Time is brain/spinal cord" in the Article "Time is Brain-Quantified", Jeffrey L. Saver, STROKE, 2006, 37: 263-266. This article also teaches that saving time will save costs, greatly reduce permanent tissue damage, and enhance near and long term quality of life. Saving time will also save lives. The Article shows us that: "Quantitative estimates of the pace of neural circuitry loss in human ischemic stroke emphasize the time urgency of stroke care. The typical patient loses 1.9 million neurons each minute in which stroke is untreated." Similarly, regardless of etiology, increased intracranial pressure (ICP) as a result of the primary injury or delays in treatment may lead to secondary (preventable) brain injury. The same applies for spinal cord compression and permanent cord injury.

Often times, a considerable amount of time elapses before the ER physician first recognizes a neurosurgical emergency in one of his/her patients, and even upon recognition, it takes a while to reach a neurosurgeon and present the case. Often times this case presentation is incomplete or inaccurate due to the inexperience of dealing with such cases. Secondary transfer of the patient to a neurosurgical center often further delays optimum non-operative immediate care. Often times in a neurosurgical emergency the precious minutes or hours lost means the difference between acceptable outcomes and permanent brain injury or spinal cord damage and a lifetime of attendant costs or early or even immediate death.

In addition, in head injured trauma, the patient often presents confounding issues with multiple other damaged organ systems (for example a splenic or liver laceration or a long-bone fracture or major peripheral vascular injury), and the trauma surgical or orthopedic or other specialty team is urgently awaiting appropriate neurosurgical clearance at continuing danger and detriment to the patient. Neurological analysis and guidance need to be much faster and more accurate.

Conversely, on occasion, neurosurgical issues are misjudged prior to proper neurosurgical consultation and the patient is rushed for emergency treatment of non-neurosurgical issues without neurosurgical clearance. In the unconscious head injured patient with no intracranial monitoring for fluctuating or raised ICP (intra-cranial pressure), this presents a considerable danger of raised untreated intracranial pressures for prolonged periods and the resultant brain injury.

In summary then, current problems and issues in neurological analysis and guidance include: Large population, many ERs, very few neurosurgeons who are not easily available; ER MDs often unfamiliar with neurosurgical case presentation to a neurosurgeon or confident about super early management, especially when there are competing emergent problems to be managed; The neurosurgeon, when reached, does not often have the information/data readily presented; Often, delays of recognition, early management, initiation of transfers to neurosurgical center occur.

SUMMARY OF THE INVENTION

The present invention is directed toward an artificial intelligence-based treatment guidance system for the neurologically impaired patient who may need neurosurgery. It aims to cut damaging, costly and sometimes even fatal time delays in delivering optimum care and a treatment plan for the patient in the Emergency Room (ER), or admitted to the hospital prior to a neurosurgeon becoming available to further direct care and intervention. The present invention also aims to help the neurosurgeon by streamlining the process of case-presentation and decision-making. Preferably, the present invention provides a fully integrated system utilizing natural language input from MD/RN (Medical Doctor/Registered Nurse) staff and interactive input interfaces for triggering and for clinical history and presentation, and utilizes automated incoming data streams from vital monitors/telemetry, clinical laboratories and radiology imaging sources for the patient concerned. In further embodiments it can also accept data streams from invasive multimodal brain monitoring equipment.

According to a first aspect of the present invention, apparatus providing medical personnel artificial intelligence (AI)-derived data regarding a patient presenting neurological indications, includes a guidance server. Preferably, the guidance server receives three or more of: (i) natural language input from medical personnel, (ii) real-time vital signs telemetry data, (iii) neurosurgical treatment database information, (iv) neurosurgical treatment guideline information, (v) clinical laboratory testing results, (vi) patient historical data, and (vii) patient imaging information. An imaging post-processor receives (i) patient imaging history information, (ii) and real-time patient imaging data, and provides to the guidance server the patient imaging information. The guidance server then provides one or more alerts (or other guidance) to the medical personnel.

According to a second aspect of the present invention, a method for providing medical personnel artificial intelligence (AI)-derived data regarding a patient presenting with neurological indications, includes receiving, with a guidance server, three or more of parameters: (i) natural language input from medical personnel, (ii) real-time vital signs telemetry data, (iii) neurosurgical treatment database information, (iv) neurosurgical treatment guideline information, (v) clinical laboratory testing results, (vi) patient historical data, and (vii) patient imaging information. An imaging post-processor receives (i) patient imaging history information, (ii) and real-time patient imaging data, and providing to the guidance server the patient imaging information. The, the guidance server providing one or more AI-generated alert(s) to the medical personnel.

According to a third aspect of the present invention, computer program code embodied in non-transitory computer readable media for providing medical personnel artificial intelligence (AI)-derived data regarding a patient presenting with neurological indications, the program comprising instructions causing at least one processor to receive, with a guidance server, three or more of parameters: (i) natural language input from medical personnel, (ii) real-time vital signs telemetry data, (iii) neurosurgical treatment database information, (iv) neurosurgical treatment guideline information, (v) clinical laboratory testing results, (vi) patient historical data, and (vii) patient imaging information. The program code also causing the at least one processor to receive, with an imaging post-processor (i) patient imaging history information, (ii) and real-time patient imaging data, and providing to the guidance server the patient imaging information. The program code also causing the at least one processor to provide, from the guidance server one or more AI-generated alert(s) to the medical personnel.

DETAILED DESCRIPTION

Figure 1:
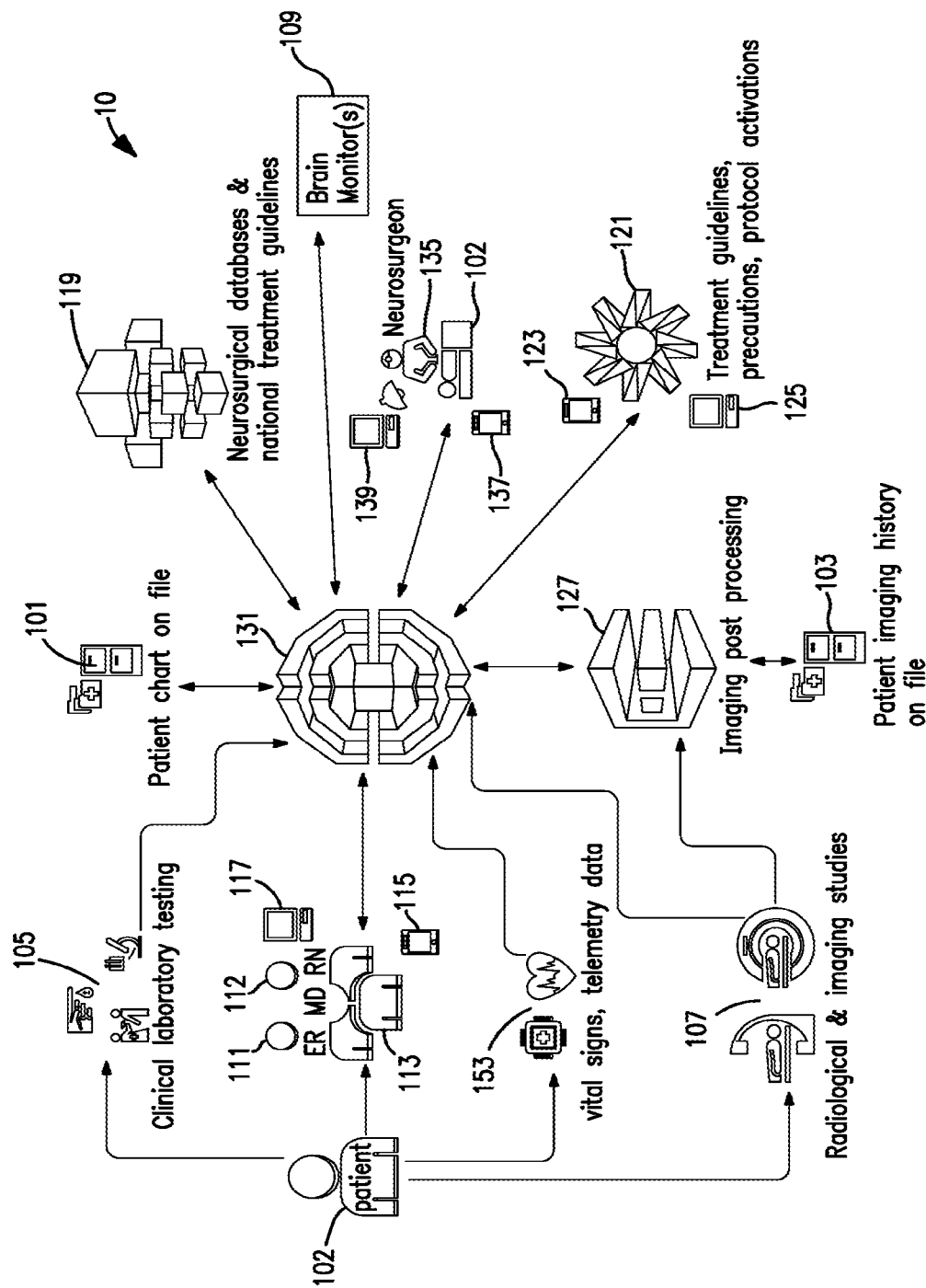
FIG. 1 is a diagrammatic illustration of the overview of the presently preferred exemplary embodiment according to the present invention.

Generally, the preferred embodiments of the present invention provide an artificial intelligence (AI) platform that utilizes nationally-recognized and accepted neurosurgical treatment guidelines, up-to-date evidence data base(s), consensus and expert opinion database(s), to provide the medical practitioner with, at least, (i) interim medical advice, (ii) further diagnostic guidelines, (iii) interim precautions, (iv) consultation recommendations, and (v) non-surgical treatment measures, at least until a neurosurgeon is available. Radiological data on the patient, in particular, may undergo post-processing for normal pattern/abnormality recognition and discrimination. Non-neurosurgical multi-disciplinary team input is also be weighed in the AI platform decision making and strategizing process.

This system, in its initial embodiment, will primarily help the ER physician with alerts and guidance until a neurosurgeon is reached. It can then present relevant data points in interactive fashion to the neurosurgeon and become a valuable tool assisting the neurosurgeon in the decision making process while he/she is still remote or on site. In further embodiments this platform can be of assistance to the neurosurgery team in the continuing inpatient setting as well as in the outpatient clinic and elective setting. This system can be broadened to cover other branches of clinical medicine and surgery with the appropriate reference databases, appropriate radiological post processing and specialty specific modifications.

As used herein, "artificial intelligence" (AI, also machine intelligence, MI) means intelligence demonstrated by machines (PCs, servers, processors, etc.), in contrast to the natural intelligence (NI) displayed by humans and other animals. In computer science, AI research is defined as the study of "intelligent agents": any device that perceives its environment and takes action(s) that maximize its chance of successfully achieving its goals. The term "artificial intelligence" is also applied when a machine mimics "cognitive" functions that humans associate with other human minds, such as "learning" and "problem solving". Capabilities generally classified as AI as of 2017 include successfully understanding human speech, competing at the highest level in strategic game systems (such as chess and Go, autonomous cars, intelligent routing in content delivery network and military simulations, etc. AI research has been divided into fields, such as particular goals (e.g. "robotics" or "machine learning"), the use of particular tools ("logic" or "neural networks"), or deep philosophical differences. AI typically uses reasoning, knowledge representation, planning, learning, natural language processing, perception, and the ability to move and manipulate objects. Approaches include statistical methods, computational intelligence, and traditional symbolic AI. Many tools are used in AI, including versions of search and mathematical optimization, neural networks, and methods based on statistics, probability, and economics. The AI field utilizes computer science, mathematics, psychology, linguistics, philosophy and many others. Currently, AI techniques are experiencing a resurgence following concurrent advances in computer power, large amounts of data, and theoretical understanding; and AI techniques have become an important part of the technology industry, helping to solve many challenging problems in computer science.

As used herein, "neural network(s)" or "logic network(s)" or "artificial neural network(s) (ANN)" are computing systems and/or devices vaguely inspired by the biological neural networks that constitute animal brains. Such systems "learn" by using artificial intelligence and/or human input (i.e. progressively improve performance on) tasks by considering examples, generally without task-specific programming. For example, in image recognition, they might learn to identify images that contain cats by analyzing example images that have been manually labeled as "cat" or "no cat" and using the results to identify cats in other images. They do this without any a priori knowledge about cats, e.g., that they have fur, tails, whiskers and cat-like faces. Instead, they evolve their own set of relevant characteristics from the learning material that they process. An ANN is based on a collection of connected units or nodes called artificial neurons (a simplified version of biological neurons in an animal brain). Each connection (a simplified version of a synapse)

between artificial neurons can transmit a signal from one to another. The artificial neuron that receives the signal can process it and then signal artificial neurons connected to it. In common ANN implementations, the signal at a connection between artificial neurons is a real number, and the output of each artificial neuron is calculated by a non-linear function of the sum of its inputs. Artificial neurons and connections typically have a weight that adjusts as learning proceeds. The weight increases or decreases the strength of the signal at a connection. Artificial neurons may have a threshold such that only if the aggregate signal crosses that threshold is the signal sent. Typically, artificial neurons are organized in layers. Different layers may perform different kinds of transformations on their inputs. Signals travel from the first (input), to the last (output) layer, possibly after traversing the layers multiple times. The original goal of the ANN approach was to solve problems in the same way that a human brain would. However, over time, attention focused on matching specific tasks, leading to deviations from biology. ANNs have been used on a variety of tasks, including computer vision, speech recognition, machine translation, social network filtering, playing board and video games and medical diagnosis. Often in an AAN, reflecting neurobiology, many inputs and input nodes converge and summate, and subsequently following processing, a smaller number of outputs emerge.

As used herein, "neurosurgery" or "neurological surgery" means the medical specialty concerned with the prevention, diagnosis, surgical treatment, and rehabilitation of disorders which affect any portion of the nervous system including the brain, spinal cord, peripheral nerves, and cerebrovascular system. Neurosurgery is often colloquially referred to as "brain surgery" though neurosurgeons often operate on the spinal cord and peripheral nervous system as well.

While the description below is given with respect to a real-time multiuser collaborative environment where there may be a plurality of users located in the room and at remote locations, other more straightforward uses may also apply without departing from the spirit or scope or the attached claims. For example, the application program may be run on a single computational device in standalone mode, or on multiple processing platforms (mobile and/or stationary). The preferred cloud/server architecture allows for a plurality of remote locations and devices to share the same workspace.

The computational devices described below devices may include one or more processors, a CPU, RAM, storage, video output, audio sound capability and the ability to connect with external peripherals, such as display(s), touch system(s), and microphone(s) and connect to an external communication network such as a hospital paging system or a cellular network, including for voice or text alerts or the World Wide Web. Preferably, the computer processor(s) are configured to read program code from one or more computer readable media (such as memory ICs, CDs, DVDs, tape, etc.). The functions described herein may be embodied in software, hardware, firmware, or any combination thereof.

A "device" in this specification may include, but is not limited to, one or more of, or any combination of processing device(s) such as, a cell phone, a Personal Digital Assistant, a smart watch or other body-borne device (e.g., glasses, pendants, rings, etc.), a personal computer, a laptop, a pad, a cloud-access device, a white board, and/or any device capable of sending/receiving messages to/from a local area network or a wide area network (e.g., the Internet), such as devices embedded in cars, trucks, aircraft, household appliances (refrigerators, stoves, thermostats, lights, electrical control circuits, the Internet of Things, etc.), and medical devices, hospital, and imaging appliances.

An "engine" is preferably one or more computer programs that performs a core function for other programs. An engine can be a central or focal program in an operating system, subsystem, or application program that coordinates the overall operation of other programs. It is also used to describe a special-purpose program containing an algorithm that can sometimes be changed. The best-known usage is the term search engine which uses an algorithm to search an index of topics given a search argument. An engine is preferably designed so that its approach to searching an index, for example, can be changed to reflect new rules for finding and prioritizing matches in the index. In artificial intelligence, for another example, the program that uses rules of logic to derive output from a knowledge base is called an inference engine.

As used herein, a "server" may comprise one or more processors, one or more Random Access Memories (RAM), one or more Read Only Memories (ROM), one or more user interfaces, such as display(s), keyboard(s), mouse/mice, etc. A server is preferably apparatus that provides functionality for other computer programs or devices, called "clients." This architecture is called the client—server model, and a single overall computation is typically distributed across multiple processes or devices. Servers can provide various functionalities, often called "services", such as sharing data or resources among multiple clients, or performing computation for a client. A single server can serve multiple clients, and a single client can use multiple servers. A client process may run on the same device or may connect over a network to a server on a different device. Typical servers are database servers, file servers, mail servers, print servers, web servers, game servers, application servers, and chat servers. The servers discussed in this specification may include one or more of the above, sharing functionality as appropriate. Client-server systems are most frequently implemented by (and often identified with) the request-response model: a client sends a request to the server, which performs some action and sends a response back to the client, typically with a result or acknowledgement. Designating a computer as "server-class hardware" implies that it is specialized for running servers on it. This often implies that it is more powerful and reliable than standard personal computers, but alternatively, large computing clusters may be composed of many relatively simple, replaceable server components.

The servers and devices in this specification typically use the one or more processors to run one or more stored "computer programs" and/or non-transitory "computer-readable media" to cause the device and/or server(s) to perform the functions recited herein. The media may include Compact Discs, DVDs, ROM, RAM, solid-state memory, or any other storage device capable of storing the one or more computer programs.

As used herein "data" and/or "data stream" means one or more of text data, image date, messaging data, audio data, video date, etc., most of which are transferred back and forth in file packages.

FIG. 1 is an overview of the system according to the presently preferred embodiments. In FIG. 1, the system 10 provides an integrated AI-based neural network type system, to continuously integrate multiple and various incoming data elements/streams regarding a patient 102, including at least: (i) patient history(s) from at least one patient chart file stored in a memory 101 and/or from patient images stored in a memory 103; (ii) physical examination records from the memory 101 and/or 103; (iii) laboratory tests results from a memory 105; (iv) radiological data (including at least 3-dimensional reconstructed scans, volumetric analyses, various fluid flow and perfusion data) stored in a memory 107; (v) brain monitoring data (if available) from brain monitor(s) 109 to provide (vi) emergency real-time push alerts and immediate clinical guidance and recommendations to the medical practitioners 111, 112, and 113 through their smartphone(s) 115 and/or PC(s) 117 on-site, based on (vii) the above-described inputs together with at least one data base and or reference base 119 of best clinical practices, neurosurgical database(s) and national treatment guidelines, best evidentiary data and the up-to-date knowledge base of common consensus amongst experts, for the neurologically impaired patient who may be a neurosurgical candidate from database(s); (viii) one or more treatment guideline database(s) 121 preferably store treatment guidelines, precautions, and protocol activations, which may be provided through one or more smart phones 123 and/or one or more PC(s) and/or pads and/or tablets 125; (ix) vital signs and patient telemetry data from one or more devices 153; and (x) the radiological and imaging data and/or imaging studies stored in memory 107, and/or the patient imaging data in memory 103 may be subject to post-processing in image post-processing processor 127. Lastly, the neurosurgeon 135 can input data (e.g., voice, text, etc.) to the guidance server 131 through one or more smartphones 137 and/or PCs or pads 139.

The patient's chart electronic health record/electronic medical record (HER/EMR), may use many different data formats, including consortium-lead interoperable standardized formats.

Health Record File Types May Include:
- ASC X12 (EDI)—transaction protocols used for transmitting patient data. Popular in the United States for transmission of billing data;
- CEN's TC/251 provides EHR standards in Europe including:
  - EN 13606, communication standards for EHR information;
  - CONTSYS (EN 13940), supports continuity of care record standardization;
  - HISA (EN 12967), a services standard for inter-system communication in a clinical information environment;
- Continuity of Care Record—ASTM International Continuity of Care Record standard;
- DICOM—an international communications protocol standard for representing and transmitting radiology (and other) image-based data, sponsored by NEMA (National Electrical Manufacturers Association);
- HL7®—a standardized messaging and text communications protocol between hospital and physician record systems, and between practice management systems
- Fast Healthcare Interoperability Resources (FHIR®)—a modernized proposal from HL7® designed to provide open, granular access to medical information;
- ISO—ISO TC 215 provides international technical specifications for EHRs. ISO 18308 describes EHR architectures;
- xDT—a family of data exchange formats for medical purposes that is used in the German public health system;

The U.S. federal government has recently issued new rules of electronic health records.

Open Specifications, Such as:
- openEHR: an open community developed specification for a shared health record with web-based content developed online by experts. Strong multilingual capability;
- Virtual Medical Record: HL7®'s proposed model for interfacing with clinical decision support systems;
- SMART (Substitutable Medical Apps, reusable technologies): an open platform specification to provide a standard base for healthcare applications.

A standardized and widely-accepted data format is used based on efficiency as well as the AI system described herein. The AI data format(s) is designed to work with one or more competing formats, as different hospitals may use different proprietary EMR software. For example, CERNER Corp. provides the widely-used EMR and uses SMART Health IT and the HL7® Fast Healthcare Interoperability Resources (FHIR®) standard.

Typically, .dcm, or DICOM files are the standard format for medical images, particularly volumetric data like CT and MRI scans. Scan data originates from and is stored briefly on the Scanner console before being uploaded by the radiology technician to the central repository system. The format can be different for each MRI scanner manufacturer. However, for clinical MRI scanners (as opposed to research MRI scanners), the most standard format for export of images is DICOM. There is no unique file extension for the DICOM format. A common one is ".dcm", but there are several other extensions that are used by the different MRI scanner manufacturers. One example of a manufacturer-specific image in DICOM format, is the ".ima" format. Each MRI scanner manufacturer will have a "DICOM Conformance Statement" that sets forth how this particular company implements the DICOM standard. Most programs that can read DICOM images will accept files with any file extension and will test whether the file is indeed in DICOM format based on the format of its content rather than on assumptions related to the file extension. Other data formats are discussed in the article "Medical Image File Formats", Michele Larobina, et al., JOURNAL OF DIGITAL IMAGING, April 2014, 27(2), 200-206.

For other file types, like 3-dimensional reconstructed scans, other useful data formats include NIfTI (Neuroimaging Informatics Technology Initiative), a standard data format used in neuroimaging to capture volumetric (f)MRI data may also be used in addition to the DICOM format. There single are (.nii) and dual (.hdr and .img) NIfTI file formats.

Clinical log data is often (or can be output as) XML file types, or other widely-used database file type formats.

The guidance server 131 integrates the various data into guidance which are, preferably distributed as alerts and clinical guidance and recommendations that are directed to the medical practitioner's personal electronic device(s) including smartphone(s) 115 and 137, and/or PC(s) and/or tablet computer(s) 117 and 139, via WiFi or cellular signal via a secure digital interface presented by a device app version of the system. The alert can take the form of a pop-up on a screen alert with (perhaps) accompanying distinct sound and/or vibration on the smartphone or electronic device or terminal screen. Preferably, clicking on the alert will direct the user to the appropriate notification page within the device app or program. Notably, if the in-app device alert is not presented for a technical reason, such as faulty device or system fault, a cellular Short Message Service (SMS) or other format of text alert can be activated as a back-up measure for critical alerts. At other times, a paging alert on the hospital's standard paging platform or a voice call may be appropriate.

Figure 2:
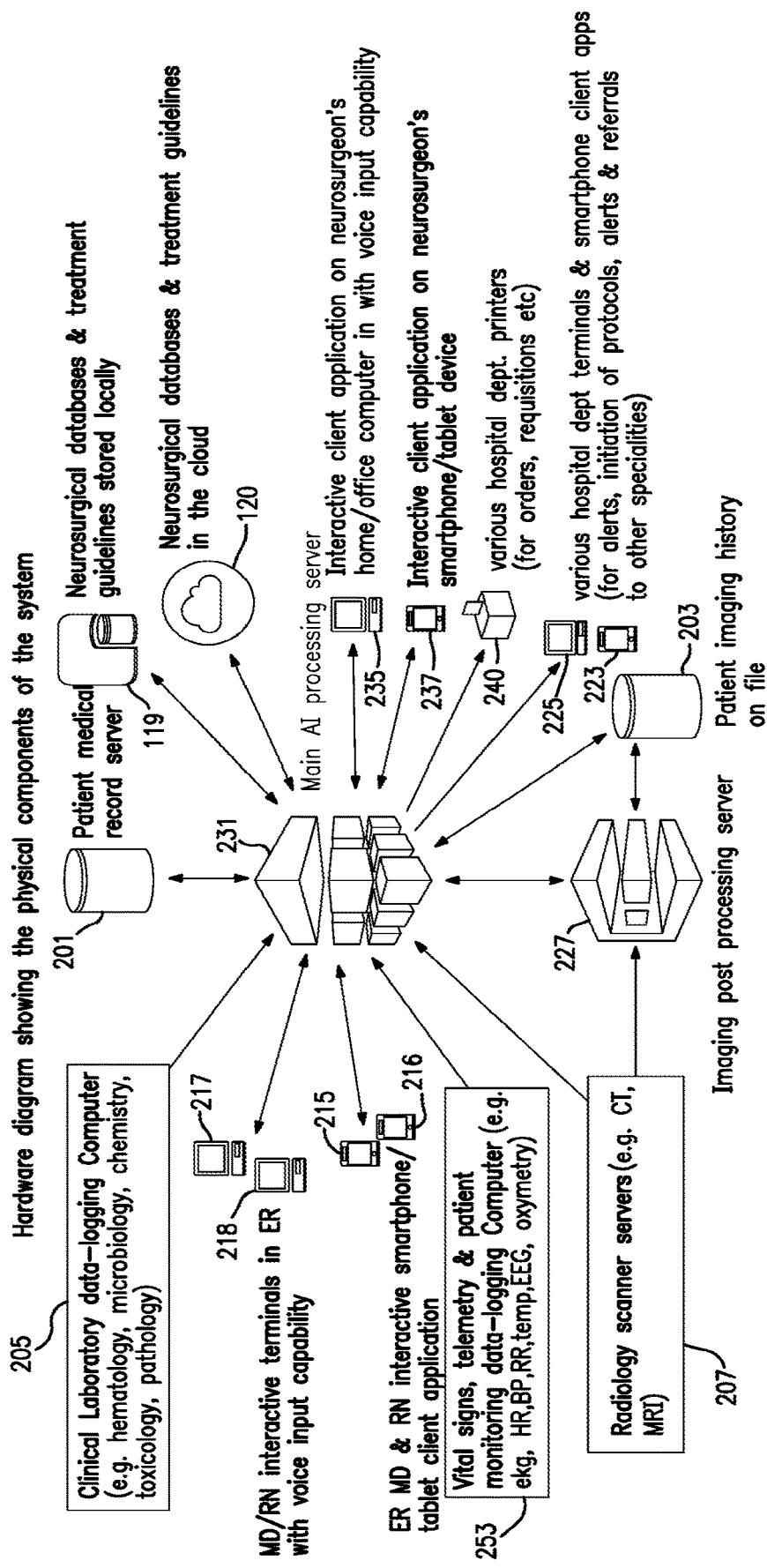
FIG. 2 is a schematic hardware block diagram according to the FIG. 1 embodiment.

FIG. 2 is a hardware block diagram of the various system components. The main AI processing server (or guidance server) 231 receives inputs from at least one clinical laboratory data-logging computer 205, the data including at least one, two, three, four or more of: hematology data, microbiology data, chemistry data, toxicology data, and pathology data. Server 231 also receives input from (and provides outputs to) MD/RN interactive ER terminals (PCs and/or pads) 217 and 218, and also to/from ER MD/RN smartphones and/or pads 215 and 216. Preferably theses ER devices have voice input and voice output capability.

Server 231 also receives inputs from at least one of vital-signs, telemetry and patient-monitoring and data-logging computer, such as one, two, three, four, or more of: Heart Rate (HR), Blood Pressure (BP), Respiratory Rate (RR), Electrocardiogram (EKG), and Electroencephalogram (EEG). Inputs are also received from one or more radiology scanner server(s) 207 (for example, Computed Tomography (CT), X-ray, Magnetic Resonance Imaging (MRI), etc.), which also provides inputs to the imaging post-processing server(s) 227. Likewise, the patient imaging history server(s) 203 provides input to (and receives output from) both the image post-processing server(s) 227 and the server 231.

One or more patient medical record server(s) 201 provides patient medical record data from the server 231, and receives output therefrom. Thus the server 231 is enabled to modify and/or update the patient's medical records. One or more neurological databases and treatment guideline servers 119 are preferably disposed locally with respect to server 231, and may even be part of the server. Server 119 receives input from (and provides output to) server 231. On the other hand, one or more neurosurgical databases and treatment guideline servers 120 may be cloud-stored, and receives output from (and provide input to) the server 231. Non-ER hospital devices may receive output from (and provide input to) the server 231, such as one, two, three, four, or more of: (i) interactive client application on neurosurgeon's home/office computer 235, preferably with voice input capability; (ii) interactive client application on neurosurgeon's home/office smartphone and/or tablet device(s) 237; (iii) one or more hospital department terminals 225 and/or tablet/smartphone device(s) 223, which preferably include one or more client apps for alerts, initiation of protocols, referrals, etc.; and (iv) one or more hospital department printer(s) and/or displays 240.

Many of the input elements, including laboratory test results and particularly radiological raw and processed data, have automated direct input integration in to the AI system 10, with continuous-flow-processing and real-time updating and real-time alert notifications and recommendations to the medical practitioner(s) once the patient has entered the processing stream. For example, such already-existing clinical and radiology network systems are network-integrated with the AI system to provide their output data in real time to the AI system. Clinical data-logging computers export their data in common file formats. For example, when the MD/RN has ordered lab tests, the AI server preferably provides a "pending result" worklist and keeps querying the clinical data-logging computer every few minutes. Alternatively, the clinical data-logging computer will auto-populate results to the AI system in the same way it does to the EMR, as and when the results roll in.

Three-dimensional reconstruction of such radiological data (including from one, two, three, four, or more of: X-rays, CT scanners, MRI scanners (including Magnetic Resonance Spectroscopy (MRS), MR diffusion tensor imaging and cerebral tractography), Positron Emission Tomography (PET) scanners, Ultrasound scanning devices and automated volumetric analyses and CT voxel radio density analyses (Hounsfield scale analysis), MRI voxel intensity analyses (incorporating tissue spatial intensity data after standardization), spinal and cranio-cervical stability analyses), are done as needed and analyzed in real-time to alert and suggest possible diagnoses and immediate treatment guidelines until such time as the neurosurgeon is reached or available to direct treatment or prepare for surgery. If the neurosurgeon is onsite, the AI system can be used as a resource to ensure nothing crucial is missed and the neurosurgeon is push-alerted automatically to his/her personal electronic device to critical update(s) in incoming patient data. In further embodiments, such 3-D reconstructions and AI analyses inform the medical staff as to elective as well as emergent, pre-operative planning, directing the surgeon towards best treatment approaches and methods based on the relative locations of normal and diseased anatomy.

Invasive (intracranial pressure, brain tissue oxygenation, cerebral blood flow) and non-invasive (EEG, cerebral oximetry, TCD) incoming brain monitoring data streams are also integrated, if the patient is already admitted and in the Intensive Care Unit (ICU), as can other incoming ICU data streams (including BP, HR, temperature, pulse oximetry, cerebrospinal fluid-drain output), etc.

In operation, in the initial stage, the system 10 is used in the emergent situation in which the neurologically impaired patient has no neurosurgeon readily available on-site (or not immediately reachable, or if reached may not be in a situation to have all relevant data immediately in front of him/her to perform the usual onsite analysis). In the last situation the system 10 directly presents pertinent information via graphics, text and natural language output to the remote neurosurgeon, via his personal electronic device (smartphone or tablet computer) as a complement to the ER physician's presentation about the case. The remote neurosurgeon then directly addresses the system 10 with natural language input, or via the interactive software platform, to query finer details or to request further processing or recommending further diagnostic or laboratory studies.

Before a neurosurgeon is available, the treating medical practitioner (most likely the Emergency Room Physician, Senior Trauma Surgeon, or neurologist) then, at his/her discretion direct immediate care needs, use applicable levels of caution, and trigger the appropriate referral and transfer priorities. This is particularly so in a multi-trauma patient who may have competing emergent needs from different damaged organ systems and when a neurosurgeon is not immediately available to provide crucial guidance, the system 10 provides the directing non-neurosurgeon physician, with appropriate guidance.

In further refinements, the integrated system may be used as an aide and guide for the neurosurgery resident and/or attending physician in emergent as well as in elective practice. In elective practice, the system 10 provides accurate and patient-specific treatment guidance, as well as outcome information to help the neurosurgeon discuss treatment alternatives as well as obtain informed consent.

There is an AI-specific standard product hub CPU (central processing unit) in the hospital (preferably within server 231), which integrates the various data streams from within the different hospital departments and performs the AI capability with online connectivity to cloud-based neurosurgery treatment reference databases. For example, a suitably high-powered server with chip lines and ASIC architecture that is dedicated to AI or favors AI can be used. For example, see the Article: "Will ASIC Chips Become The Next Big Thing In AI?", Karl Freund, Forbes Magazine, Aug. 4, 2017. There can also be a locally stored version of the treatment databases which can be updated from the cloud routinely. The AI hub does the notifying, push, alerting, and sharing during the workflow. The data streams are preferably integrated by combining the history and presentation from the MD/RN and any old EMR reports on file. Preferably, new and old key imaging findings are integrated, and using key words, create: a likely-problem list, laboratory tests-to-order, results to watch out for, treatment sieves through which possible diagnoses pass, and/or address critical dangers.

Thus, the AI server 231 and system 10: (i) streamlines data gathering of different diagnostic elements and patient history and examination; (ii) ensures pertinent facts/data are not missed or overlooked or delayed in being looked at; (iii) efficiently presents to the neurosurgeon when available; (iv) provides problem discrimination and problem weight criteria (e.g., neurosurgical and non-neurosurgical issues using a common mathematical framework); (v) performs pattern-recognition and further imaging processing to provide added information to decision making and alerting process; (vi) uses neurosurgical treatment guidelines and databases to give ER MD initial guidance on medical treatments, precautions, referrals and transfer protocols; and pushes alerts of important and urgent findings.

Figure 3:
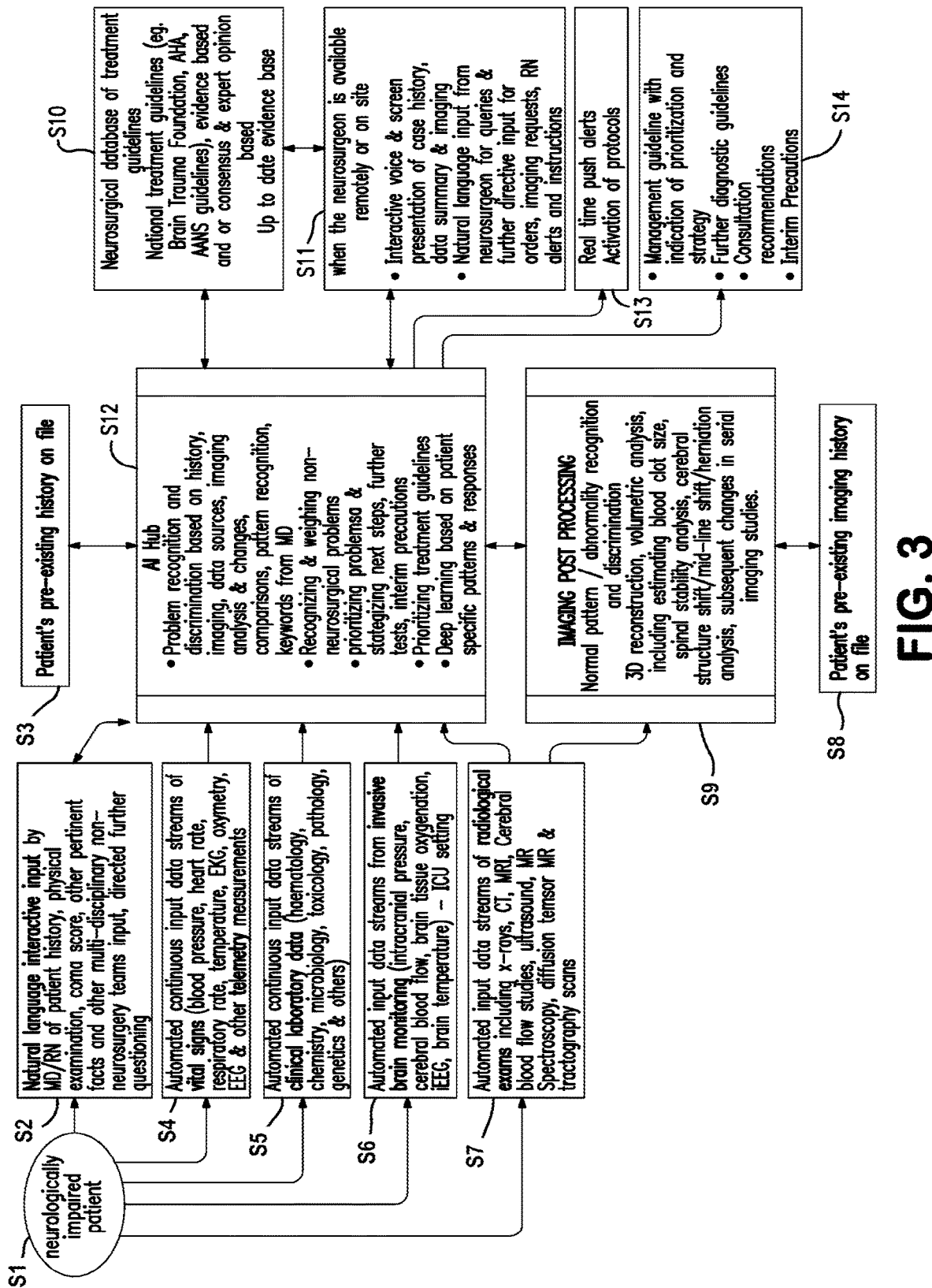
FIG. 3 is a flowchart according to methods of the FIG. 1 embodiment.

With reference to the functional flowchart of FIG. 3, the processes and methods described therein are be performed by the various servers (including server 231) and/or devices described above. When a neurologically impaired patient is brought to the ER in Step S1, the ER staff will immediately (Step S2) attempt to ascertain a medical history (including neurological history; Step S3) while simultaneously starting to assess the patient's vital signs (e.g., heart rate, blood pressure, temperature, respiratory rate and often immediately place the patient on telemetry monitoring for EKG and the earlier mentioned vitals). The ER physician will do a quick physical examination and a more focused neurological examination as it would be deemed necessary in this instance. Most, but not all, ER physicians will be able to deduce a mostly accurate Glasgow Coma Score, others would be able to do it with proactive prompting and basic step by step live guidance. Often times, specific neurological tests or measurements (peripheral neurological reflex testing, pupil size and changes to light, corneal/gag reflexes etc.) are not checked by ER staff in the rush.

In Step S2, the MD/RN provides a natural language interactive input into system 10 (preferably by voice) of one, two, three, or more of the patient history, physical examination, coma score, other pertinent facts, and/or other multi-disciplinary non-neurosurgeon team inputs with directed further questioning.

The patient is often rushed to the CT scanner for a plain CT scan of the head to look for an abnormality following significant trauma or unexplained neurological impairment. Early laboratory tests (blood, urine, drug levels and others based on history) are often drawn and sent to the clinical labs. If an ischemic stroke is suspected and MRI scanning is available, an early MRI scan is also sometimes arranged.

The CT scan is read by an onsite or remote radiologist in due course and reported. The radiologist will call in an urgent finding to the ER MD generally but may not get to reading it in the first place right away. The ER physician keeps checking manually on the different pending tests and scan results and based on his interpretation will consult a neurologist or neurosurgeon at the hospital or attempt to consult an on-call one available remotely. Other patients coming in and ongoing and new emergencies with other patients often keeps the ER MD busy and having to multi-task while the neurologically impaired patient (who is almost by definition the "quiet patient") remains in the background with different pending results.

Meanwhile, if abnormal lab results or lab results dangerous to the present condition of the patient are reported, (for example an anticoagulated blood profile, a raised INR or a PTT lab value, or a low platelet count in the presence of a brain hemorrhage) they will have to be appropriately corrected as soon as possible. The lab technician may call in critical values to the ER MD but then too there is often a delay and a value not deemed critical in a regular patient may be super critical in a patient with a neurosurgical issue (a low platelet count for instance).

If the patient was on medications previously and they are known, another task arises to cross reference the possible on-going neurosurgical situation with those medications and check if any immediate remediation is required. The ER MD will typically do this but the alert, depending on scan and lab results and the remediation can delayed be frequently.

The status quo system universally keeps the entire treatment path fully dependent on the test and scan results being checked on at the earliest instance and acted on immediately. This may not happen on the most optimal possible timeline in a real life ER for any number of reasons. With every passing second/minute, a patient with a brain hemorrhage for instance, (and in a patient on blood thinners or platelet inhibitors for a more aggravated critical example) a rising intra cranial pressure will only keep getting worse and have an exponentially poorer outcome and increased mortality with time.

Even when the ER MD successfully reaches the neurosurgeon on call, the case is often presented in haphazard fashion from the neurosurgeon's perspective and various key data elements are not readily presented or easily accessible to the neurosurgeon. This often has the neurosurgeon trying to ascertain further details and the accuracy and pertinence of the case laid out, adding to the delay.

The integrated artificial intelligence based platform (called ANVer1 herein), greatly speeds up the data integration. At the point of the medical staff making contact with the neurologically impaired patient, the ER MD or RN can trigger AI assistance on this patient's care by using his or her personal electronic device; a tablet or smart phone device running the client application of the system.

From that point onwards all data elements normally generated as part of the normal clinical diagnostic processes can be automatically be directed to be streamed in to the AI system 10 (e.g., the server 231) as and when they become available in real time. This would include all vital signs and telemetry data, all clinical laboratory data, all imaging and radiology data. In other embodiments, where this AI system 10 is used on inpatients, this can also include multimodal invasive brain monitoring data. As it stands in the United States and most other advanced countries, all of this data is already generated in a digital format and most of it frequently used to populate the patient's computerized clinical chart automatically. Having each of these hospital departments and entities run a digital link to the artificial intelligence system server 231 employs a relatively straightforward network connection and interface.

At the time of triggering, the ER RN and MD also uses natural language input to voice a brief history and clinical examination and use key words and phrases to mark out pertinent facts about the case, clinical suspicions, possible diagnoses, diagnoses that need to be ruled out. Key word and phrase recognition directs the working 'hot list' of problems/diagnoses (to be discussed below).

The AI system is preferably connected to the databases discussed above, which are stored on servers locally as well as in the cloud, of neurosurgical diagnostic pathways, attendant precautions, treatment guidelines, and nationally recognized treatment protocols. Key word and phrase recognition is used to begin the process of problem discrimination, compose a list of possible differential diagnoses, and diagnosis elimination as laboratory and imaging test begin to stream in.

The initial RN/ER MD with AI encounter is interactive and based on key words and phrases, the AI system can offer helpful pointers in real-time to the ER MD about what to look out for, guidance about what to further examine, what clinical tests need to be performed, and/or further recommended imaging or laboratory testing. This guidance is a combination of verbal and/or textual and/or graphical presentation. For certain tests or to determine certain objective clinical scores like the Glasgow Coma Score the system can even guide the medical practitioner through it to ensure further accuracy and to ensure all of the most important data elements are available for the neurosurgeon.

Using natural language input, the ER physician or other non-neurosurgical multi-disciplinary teams members involved (such as the trauma-surgical or orthopedic team) can further input in to the AI system using a simple grading system the severity and urgency of injuries relevant to their specialty.

A simple 0-10 grading system of severity and urgency based on how long that particular non-neurosurgical injury can be left untreated in the face of grave neurosurgical issues provides a mathematical framework for the AI system to help problem weigh, strategize, and prioritize in its guidance output. For example, in a poly-trauma patient with a severe/critical head injury, a ruptured spleen or a massive liver laceration or a tension pneumothorax would rate as extremely critical, i.e., 10/10 and extremely urgent, 10/10 non-neurosurgical injury; while a dislocated shoulder would be important to fix 5/10, but not urgent, given the context 2/10. A large, open long-bone fracture is critical to fix 10/10 and urgent 7/10, but not immediately life-threatening. National trauma surgical and orthopedic guidelines are used to develop an acceptable conforming grading system.

Returning to FIG. 3, at Step S4, automated and continuous input of data streams of vital signs (e.g., one, two, three, four, or more of blood pressure, heart rate, respiratory rate, temperature, EKG, oximetry, EEG, and other telemetry measurement data) are provided to the server 231. In Step S5, automated and continuous input of data streams of clinical laboratory date (e.g., one, two, three, four, or more of hematology, chemistry, microbiology, toxicology, pathology, genetics, etc.) are provided to the server 231. Likewise, in step S6, automated and continuous input of data streams of invasive brain monitoring data (e.g., one, two, three, four, or more of intracranial pressure. Cerebral blood flow, brain tissue oxygenation, internal ElectroencEphaloGraphy (EEG), non-invasive external EEG, brain temperature, if the patient is in an ICU setting, are preferably provided to the server 231. Further, in Step S7, automated and continuous input of data streams of radiological exams (e.g., one, two, three, four, or more of X-rays, CT, MRI, Cerebral blood flow studies, ultrasound, MR Spectroscopy, diffusion tensor MR, and/or tractography scans) are provided to the server 231.

In FIG. 3, Step S7 also provides input data to the image post-processing Step S9, which also receives input data from the patient's pre-existing imaging history file, in Step S8. Step S9, inputs into the server 231 one, two, three, four, or more of normal-pattern/abnormal-pattern recognition and discrimination data, 3D reconstruction data, volumetric analysis data, estimated blood clot size data, spinal stability analysis data, cerebral structure shift/midline shift/herniation analysis data, and/or subsequent changes in serial imaging studies data.

In Step S10, data input to the server 231 may comprise one, two, three, four, or more of neurological database treatment guidelines, national database treatment guidelines (e.g., from the Brain Trauma Foundation, the American Heart Association (AHA), the American Association of Neurological Surgeons (AANS) guidelines), up-to-date evidence-based study data, consensus opinion data, and/or expert opinion data. Of course, the server 231 may also provide input to these databases. Note that the AHA produces important cerebrovascular stroke guidelines, with neurosurgeons on their advisory board or neurosurgeons directly writing these guidelines. These AHA guidelines are used by neurosurgeons too.

In Step S11, when the neurosurgeon is available on-site or remotely, data input to the server 231 may comprise one, two, three, four, or more of interactive voice and screen display presentation data of the patient case history, data summaries, imaging data, natural language input data from the neurosurgeon for queries and for further directive input for orders, imaging request, RN alerts, and instructions. Again, the server 231 may also provide input to these databases.

At Step S12, the sever 231 preferably inputs the above-described data and provides the AI system analysis/calculations/data-formatting/etc. used to perform one, two, three, four, or more of: (i) problem-recognition and discrimination based on history, imaging, data sources, imaging analysis, changes, comparisons, pattern recognition, and/or keywords from the MD [for example, key words/phrases like: loss of consciousness following "sudden headache", "anisocoria", different size pupils following "trauma", "seizure", etc.]; (ii) recognizing and weighing non-neurological problems [for example Splenic rupture following trauma, extremely critical and extremely urgent, etc.]; (iii) prioritizing problems and strategizing (triage) for next steps, further tests, and/or interim precautions [for example unstable c-spine fracture would necessitate patient movement, bracing and handling precautions, blood in the brain on scan following trauma would necessitate seizure precautions and seizure drug prophylaxis]; (iv) prioritizing treatment guidelines [for example, evidence of raised intra-cranial pressure, prioritizing urgent medical treatment with mannitol or hypertonic saline to prevent brain herniation and death]; and/or (v) deep-learning based on patient-specific patterns and responses [for example, in further embodiments of the system for inpatients, some patients tend to have recurrent problems that are infrequently seen in others, e.g., diabetes insipidus following pituitary surgery, or cerebral vasospasm following subarachnoid hemorrhage or trauma, or seizures following trauma, so having one episode will make the AI system doubly watch out for or proactively check for recurrent episodes].

After (or during) Step S12, the server may output data to any of the steps described above in an interactive, feed-back system meant to refine analysis and diagnoses until acceptable solutions/decisions may be made. Of particular importance are data outputs as real-time push alerts to the smart-phones, tablets, pads, and/or PCs of the relevant medical personnel, such as the ER MDs and RNs, at Step S13 [for example, a super critical hematological laboratory result, a very high INR (international normalized ratio) or a blood clotting issue in someone with a brain hemorrhage, or a large blood clot on a screening CT head scan]. At Step S14, the server 231 provides data input to one, two, three, four, or more of management guidelines with indication of prioritization and strategy, further diagnostic guidelines, consultation recommendations, and/or interim precautions [for example, correcting blood pressure carefully in the setting of possible aneurysmal subarachnoid hemorrhage, giving activity precautions for the same reason].

Figure 4:
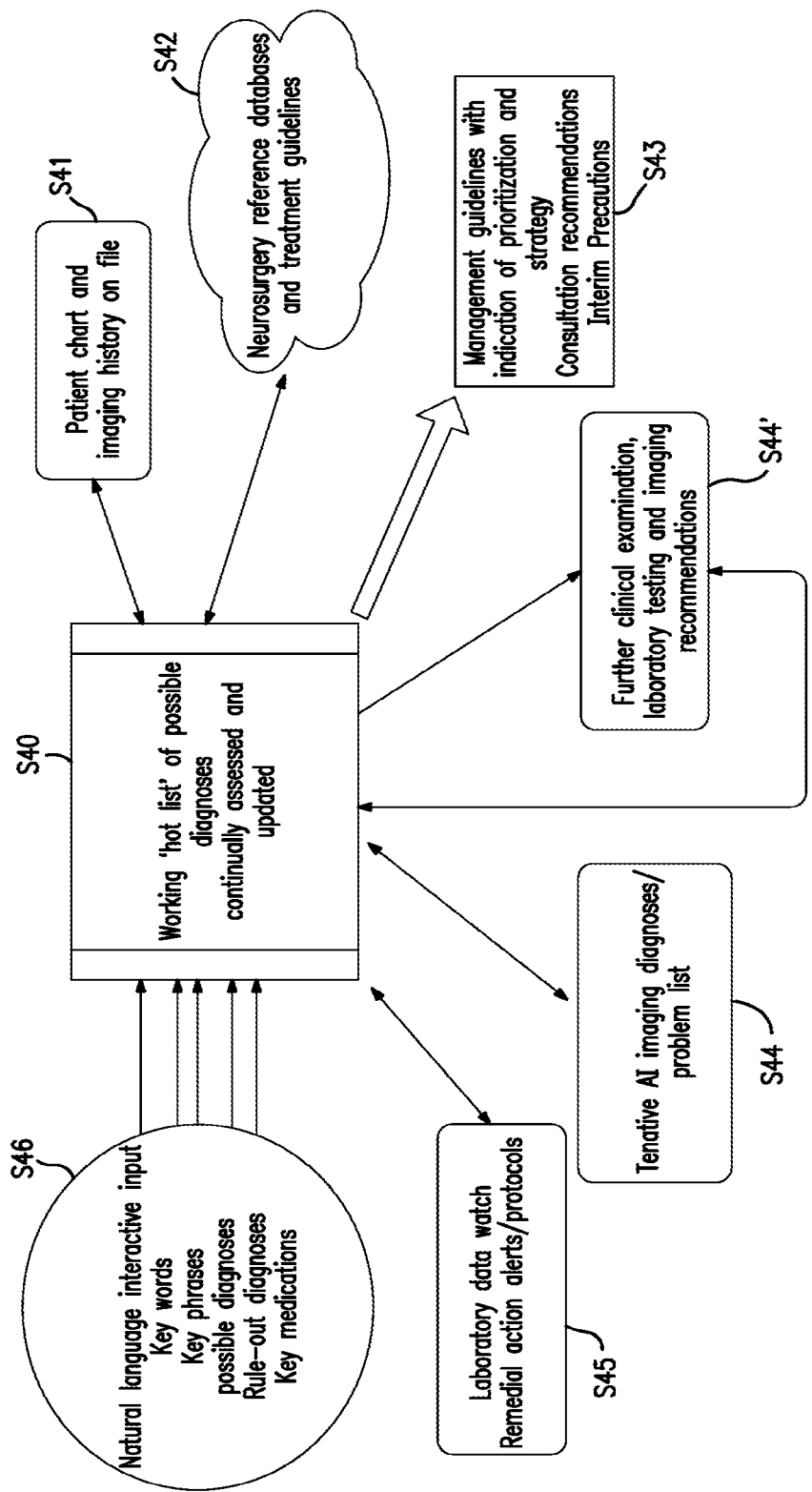
FIG. 4 is a functional diagram of hot-list management, according to the FIG. 1 embodiment.

As the possible diagnoses become available based on the key words and phrases and/or imaging findings, the AI system 10 develops and maintains a working 'hot list' of possible diagnoses and problems, as depicted in FIG. 4. [for example, for sudden loss of conscious without trauma, the following would be on a "hot list" of possible important diagnoses to rule out: seizure, embolic stroke, hemorrhagic stroke, TIA (transient ischemic attack), and/or for blood on the head, trauma, aneurysmal subarachnoid hemorrhage, vascular malformation, hemorrhagic brain tumor]. The working 'hot list' also allows the AI system 10 to provide suggestions to the ER MD and direct further relevant discriminative clinical, laboratory, and/or radiological testing, to help narrow down the diagnosis quicker than waiting for input from a neurosurgeon.

In FIG. 4, automated cross referencing of previous medications and incoming laboratory data is performed to ensure dangerous lab values, given the context of the current situation, are not missed (e.g. thrombocytopenia) and/or if any previously-taken medications need remedial action (e.g. reversing anti-platelet therapy in a brain-hemorrhage setting). Vital signs and telemetry data are also be monitored for outlying values, changes, and trends. Nursing and physician updates to the neurological examination are also integrated on an ongoing basis.

In FIG. 4, in Step S41, the patient's preexisting medical record, including key medical conditions, medications, and pre-existing imaging data and reports are inputted to the server 231 at Step S40, to determine the "hot list." These inputs provide a basis for added input for problem discriminating by the AI system 10. In Step S42, data from neurosurgery reference databases and treatment guidelines are also used in Step S40 to determine the "hot list." In Step S43, the Step S40 provides "hot list" data to management guideline databases, preferably with an indication of prioritization and strategy. Likewise in Step S43, "hot list" data is provided to display/utilize/store consultation recommendations and interim precautions.

In Step S44', a feedback loop is established with Step 40 whereby further clinical examination, laboratory testing, and imaging recommendations are provided for the care-giver. In Step S44, tentative AI imaging diagnoses/problem lists are determined, in conjunction with Step S40, to provide real-time information to the care-givers. In Step S45, the AI system 10 provides laboratory data watch and remedial action protocols, to the Step S40 and to the care-givers. In Step S46, natural language interactive input from the care-givers is provide to Step S40, such as key words, key phrases, possible diagnoses, rule-out diagnoses, an/or key medications.

Figure 5:
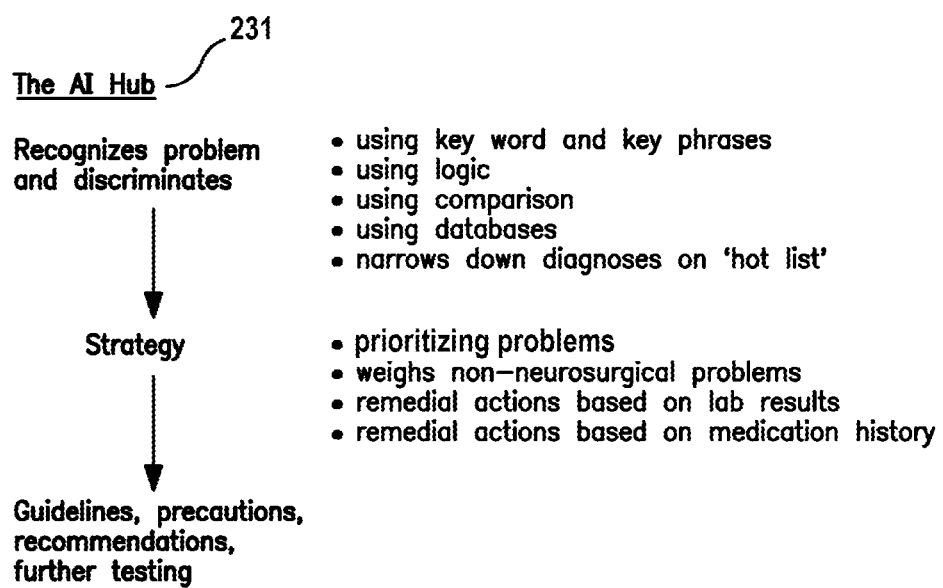
FIG. 5 is a schematic showing the functions of the AI hub, according to the FIG. 1 embodiment.

In FIG. 5, an important component of the system 10 is the AI co-processing hub 127, 227 for radiological and imaging data. As mentioned previously, 3-dimensional reconstruction of radiological data is performed, as needed, to better analyze space-occupying intra-cranial lesions and well as assess cranio-cervical stability as well as spinal stability. CT voxel radio-density analyses (different tissues, bone, and blood have different values of radio-density as measured on the Hounsfield scale for example) of the CT scan image, in combination with pattern recognition, variation from normal and abnormality detection is incorporated in to the post-processing to develop an AI-based tentative reading of the study, and alerts the ER MD (as well as the radiologist) to a major significant possible finding.

Similar AI based software processing of MRI scans with voxel intensity analyses (incorporating tissue spatial intensity data after standardization) as well as analyses of different MRI sequences (T1, T2, DWI, GRE etc.) is used in combination with pattern recognition, variation from normal and abnormality detection for post-processing to develop an AI based tentative reading of the study and once again alert the ER MD as well as the radiologist to a major significant possible finding.

3-dimensional reconstruction of CT scans of the craniocervical junction and spinal column, along with digital plain X-ray studies are used with structural modeling software to assess stability. MRI evidence of any ligamentous injury is incorporated into this analysis as and when available. The AI based analysis of this can then tentatively warn of precautions as well as provide management guidelines until the neurosurgeon has review the entire case based on current nationally accepted spinal injury and management protocols. The neurosurgeon may use it as a cross reference tool, as well in further embodiments of the system once confidence has been established.

In FIG. 5, the AI hub 231 recognizes a problem and discriminates among the numerous variables presented by that problem, based on predetermined AI criteria [for example, based primarily on key words and phrases, rule-out diagnoses, problem list(s) based on the ER MD's presenting complaint list, history, and presentation and key imaging findings; an ER MD in his or her usual work-flow would likely produce a brief or more extensive written, computerized or dictated record of the presenting history, examination, and clinical findings, problem list and rule out diagnoses on predetermined AI criteria]. The AI hub performs this problem identification and discrimination function using the natural language key words and phrases, logic, comparisons with prior related problems, and databases of known problems with solutions, along with data received from the radiology hub. From these functions and databases, the AI hub narrows down the possible diagnoses for the problem to a "hot list" of most-likely problems and attendant solutions. After narrowing the problem/solution list, the AI hub develops a strategy for providing effective guidance to the medical staff. In particular, the AI hub prioritizes the "hot list" problems based on criteria such as: what is important to rule-out (e.g., urgent, dangerous diagnoses that may be possible given the context and would be dangerous to miss); what is most likely based on incoming clinical and radiological data and statistics and the ER MD's problem list and other triggering words and phrases. Precise criteria currently exist in nationally recognized and accepted treatment guidelines and consensus opinions for most neurosurgical conditions.

As one example of such guidelines, see the U.S. Department of Health and Human Services Agency for Healthcare Research and Quality (AHRQ) National Guideline Clearinghouse, "Neurological Surgery", July 2018. This Federal document is a good summary of publicly available online guideline for neurosurgery, used in the preferred embodiments.

Some notable individual guidelines which are widely used in practice include the following. All of the guidelines and protocols discussed herein (and others), are used in the preferred embodiments, and are incorporated herein by reference. These are publicly available documents and do not need to be licensed for use. The contents are coded into reference database(s) noted above.

The Brain Trauma Foundation "Guidelines for the Management of Severe Traumatic Brain Injury 4th Edition", Nancy Carney, et al., September 2016, also incorporated herein by reference. This is an accepted nationwide as standard of care, Reviewed for evidence-based integrity and endorsed by the American Association of Neurological Surgeons and the Congress of Neurological Surgeons.

The American Heart Association Stroke guidelines, "2018 Guidelines for the Early Management of Patients With Acute Ischemic Stroke: A Guideline for Healthcare Professionals From the American Heart Association (AHA)/American Stroke Association (ASA)", William J. Powers, et al., January 24.

AHA/ASA guidelines, "Clinical Resources and Tools", May 2018.
AHS/ASA "Direct to CT/MRI Protocols", October 2014.
AHA/ASA "Patient Time Tracker", 2014.
Congress of Neurological Surgeons "Complete Guidelines", 2018.
American Association of Neurological Surgeons and the Congress of Neurological Surgeons, "New Brain Metastases Treatment Guidelines", Published in the Journal of Neuro-Oncology, Dec. 2, 2009.

In neurosurgery there is a very convenient handbook that is also available in electronic format called the "Handbook of Neurosurgery", by Mark S Greenberg, et al., 2006 that summarizes all the guidelines and current consensus opinions from different sources and publications. This handbook is the defacto reference bible in actual practice in neurosurgery in the US and around the world. In the actual implementation of this system, that book is also used as a convenient guide in the above-described reference databases.

The above-noted criteria, guidelines, database(s) are used as a basis of the for the disclosed AI system. The AI hub weighs non-neurosurgical problems, determines remedial actions based on lab results, and determines remedial actions based on their medication history. Once the strategic functions are determined, the AI hub outputs one or more reports and/or alerts and/or protocols providing to the medical staff appropriate treatment guidelines, precautions, recommendations, and options for further testing and/or treatment. Such reports are provided by text, video, oral, image, and/or mixed media. For example, the output screen has different boxes/screen areas with varying size text and titles and hyperlinks and actionable links, such as AI-directed further investigation list(s), AI-directed further clinical examination list(s) and/or walk-through sequences, an AI generated problem and diagnosis list, AI generated radiology report, Treatment guidelines, Warning(s), Alert(s), Precaution(s), Recommendation(s), Consultation(s), and/or other options, such as Direct Messaging options to/from neurosurgeon and/or other health care professionals, various hospital protocol triggering actions, etc.

Figure 6:
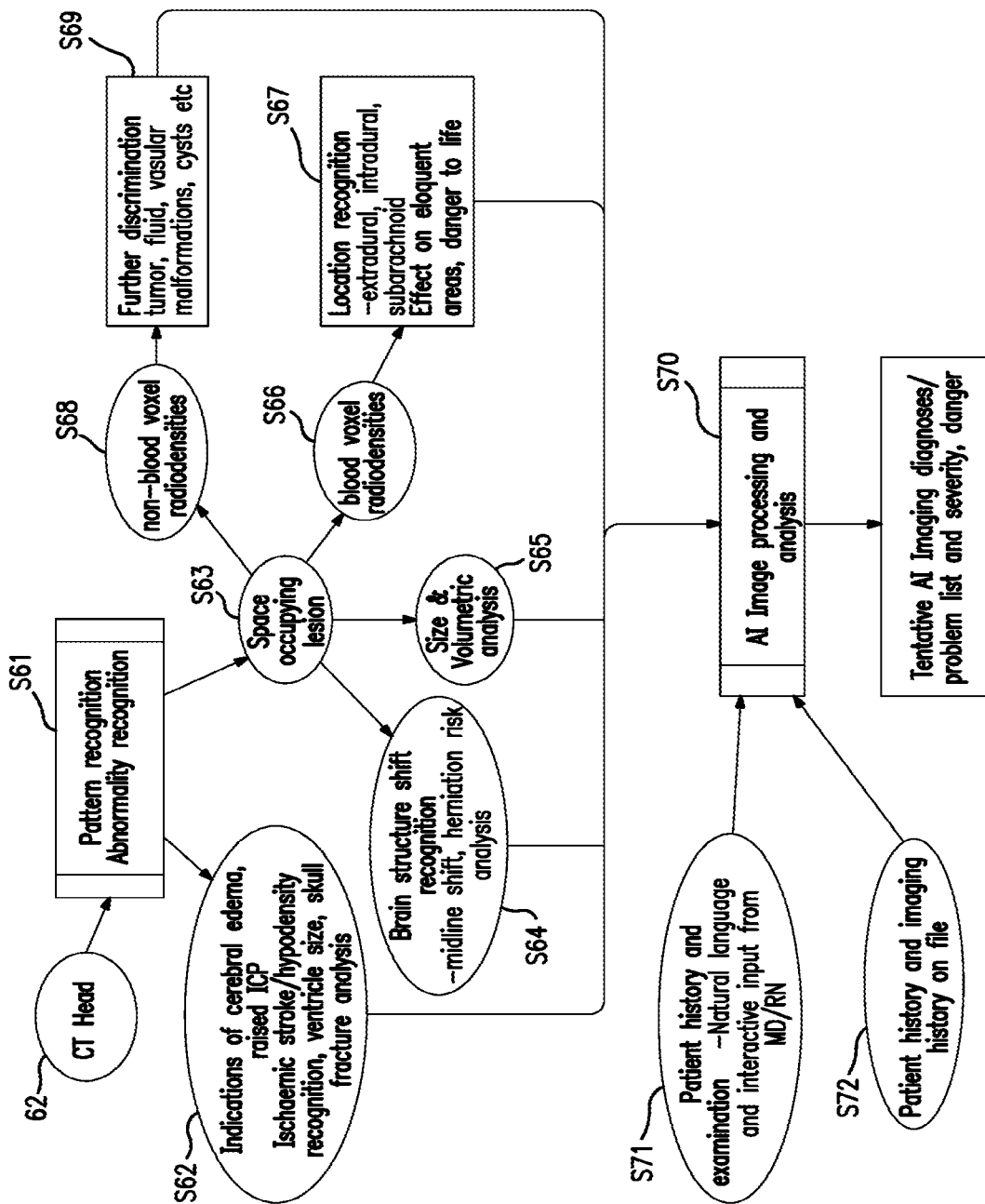
FIG. 6 is a functional diagram of a simple example of Imaging AI Problem Processing, according to the FIG. 1 embodiment.

FIG. 6 is a functional diagram of a simple example of Imaging AI Problem Processing, according to the FIG. 1 embodiment. These functions are preferably performed by one or more processors associated with the AI hub 227, although these functions could be performed in one or more associated processors, like the guidance server 231. For example, in the case of a patient receiving a CT scan for a neurological deficit or significant complaint, the AI imaging hub 227 first performs pattern recognition for abnormality recognition, in Step S61. In Step S62, if there are indications of one or more of cerebral edema, raised ICP, ischemic stroke/hypo density recognition, ventricle size anomalies, indications of skull fracture analysis, the process proceeds to step S70. In step S70, the AI hub 227 performs the required AI image processing and analysis.

Returning to step S61, if a space-occupying lesion is detected at Step S63, the AI hub 227 determine whether (i) a brain structure shift has been recognized in Step S64 (e.g., a midline shift, and/or herniation risk analysis), (ii) size and volumetric analysis indicates a potential problem and its extent, at Step S65, and/or (iii) whether voxel radiodensities indicate blood and if it is acute or chronic blood, (iv) (Step S66) indicates location recognition (e.g., extradural, intradural, and/or subarchnoid), effect(s) on eloquent areas, and/or danger to life need to be considered, at Step S67. Meanwhile, Step S63 can also determine that non-blood voxel radiodensities (Step S68) indicate that further discrimination of tumor, fluid, vascular, malformations, cysts, etc. need to be performed (Step S69).

Following one or more of Steps S62, S64, S65, S67, and/or S69, the AI hub 227 performs the AI image processing and analysis at Step S70. During this processing, the AI hub also receives input from the patient history and examination, preferably in natural language and interactive input from the MD/RN, at Step S71. Likewise, Step S72 provides to the AI hub the on-file patient history and imaging history. The output of the AI image processing produces a tentative AI imaging diagnosis/problem-list, along with corresponding severities and/or dangers.

As AI system analyses are done in real-time as data elements become available, alerts, suggestions of possible diagnoses, and immediate treatment guidelines are presented to the ER MD until such time as the neurosurgeon is reached or available to direct treatment or prepare for surgery. If the neurosurgeon is onsite the system is use as an information resource to ensure nothing crucial is missed and the neurosurgeon is push-alerted automatically to his/her personal electronic device of any critical update in the incoming patient data.

As mentioned earlier, in other embodiments of the system, invasive (intracranial pressure, brain tissue oxygenation, cerebral blood flow, intracranial EEG) and non-invasive (EEG, cerebral oximetry, TCD) incoming brain monitoring data streams are preferably integrated as automated continuous inputs into the system if the patient is already admitted and in the ICU. This is done with other incoming ICU data streams (including BP, HR, temperature, pulse oximetry, cerebrospinal fluid-drain output) as well. In this embodiment, the AI platform acts as a comprehensive guide and assistant to patient management and for patient specific guidance and as a reference of best management practices.

The individual components shown in outline or designated by blocks in the attached Drawings are all well-known in the electronic processing arts, and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A system providing artificial intelligence (AI)-based diagnostic guidance for a patient, comprising:
one or more radiology scanners for scanning a body portion of the patient and to capture radiological scan images of the body portion of the patient,
an imaging post-processor connected to the radiology scanners to receive the captured radiological scan images of the patient and connected to one or more patient imaging history servers to receive patient imaging history information; and
an AI hub connected to the radiology scanners to receive the captured radiological scan images of the patient, wherein the AI hub is configured to receive input data comprising one or more selected from the group consisting of (i) natural language input data received from an Emergency Room (ER) terminal or an ER device of medical personnel, (ii) real-time vital signs telemetry data of the patient received from a patient monitoring and data-logging computer, (iii) clinical laboratory testing results data of the patient received from at least one clinical laboratory data-logging computer, and (iv) patient historical data of the patient received from one or more medical record server,
wherein the imaging post-processor is configured to perform:
recognizing patterns of the received radiological scan images of the patient to detect abnormality;
reconstructing the received radiological scan images of the patient into three-dimensional reconstructed scans;
generating patient imaging information based on the recognized patterns of the received radiological scan images of the patient and the three-dimensional reconstructed scans; and
providing the AI hub with the patient imaging information; and
wherein the AI hub is configured to perform:
identifying problems, based on predetermined AI criteria and deep-learning based on patient-specific patterns and responses, by using one or more selected from the group consisting of natural language key words and phrases, logic, comparisons with prior related problems, databases of known problems with solutions, the patient imaging information, and the input data;
prioritizing the problems to a hot list based on what is important to rule-out and what is most likely based on the patient imaging information and the input data; and
providing medical staff with AI-generated interim diagnostic alerts and/or guidance based on the identified and prioritized problems.

2. The system of claim 1 wherein the AI hub is connected to one or more neurosurgical database and treatment guideline servers that include the national treatment guidelines, and wherein the one or more severs are configured to receive one or more selected from the group consisting of (i) neurosurgical treatment database information and (ii) neurosurgical treatment guideline information from the one or more neurosurgical database and treatment guideline servers.

3. The system of claim 2 wherein the AI hub is further configured to provide the interim medical advice and the diagnostic guidelines based on the national treatment guidelines.

4. The system of claim 1 wherein the AI hub is configured to receive up-to-date evidence data, consensus opinion data, and/or expert opinion data.

5. The system of claim 1 wherein the AI hub is further configured to provide one or more alerts and/or suggestions for diagnoses and immediate treatment guidelines.

6. The system of claim 5 wherein the AI hub is configured to provide the medical staff including a neurosurgeon, neurologist, specialist with the one or more alerts and/or suggestions by data stream.

7. The system of claim 5 wherein the AI hub is configured to provide the one or more alerts and/or suggestions to the medical staff including the neurosurgeon, neurologist, specialist onsite or at a remote location.

8. The system of claim 1 wherein the AI-based diagnostic guidance is for a patient presenting with neurological indications including but not limited to one or more of cerebral edema, raised intracranial pressure (ICP), ischemic stroke/hypo density recognition, ventricle size anomalies, indications of skull fracture, decompensating tumors, hemorrhagic and large ischemic stroke, and post-operative decompensation.

9. A method for providing artificial intelligence (AI)-based diagnostic guidance for a patient, comprising:
scanning a body portion of the patient and capturing, by using one or more radiology scanners, radiological scan images of the body portion of the patient;
receiving, via an imaging post-processor and an AI hub, the captured radiological scan images of the patient;
receiving, via the AI hub, input data comprising one or more selected from the group consisting of (i) natural language input data received from an Emergency Room (ER) terminal or an ER device of medical personnel, (ii) real-time vital signs telemetry data of the patient received from a patient monitoring and data-logging computer, (iii) clinical laboratory testing results data of the patient received from at least one clinical laboratory data-logging computer, and (iv) patient historical data of the patient received from one or more medical record server;
recognizing, via the imaging post-processor, patterns of the received radiological scan images of the patient to detect abnormality;
reconstructing, via the imaging post-processor, the received radiological scan images of the patient into three-dimensional reconstructed scans;
generating, via the imaging post-processor, patient imaging information based on the recognized patterns of the received radiological scan images of the patient and the three-dimensional reconstructed scans;
providing the AI hub with the patient imaging information;
identifying, via the AI hub, problems, based on predetermined AI criteria and deep-learning based on patient-specific patterns and responses, by using one or more selected from the group consisting of natural language key words and phrases, logic, comparisons with prior related problems, databases of known problems with solutions, the patient imaging information, and the input data;

prioritizing, via the AI hub, the problems to a hot list based on what is important to rule-out and what is most likely based on the patient imaging information and the input data; and providing medical staff, via the AI hub, with AI-generated interim diagnostic alerts and/or guidance based on the identified and prioritized problems.

10. The method of claim 9 further comprising receiving, via the AI hub, one or more selected from the group consisting of (i) neurosurgical treatment database information and (ii) neurosurgical treatment guideline information from one or more neurosurgical database and treatment guideline servers that include the national treatment guidelines.

11. The method of claim 10 wherein the AI hub is further configured to provide the interim medical advice and the diagnostic guidelines based on the national treatment guidelines.

12. The method of claim 9 further comprising receiving, at the AI hub, up-to-date evidence data, consensus opinion data, and/or expert opinion data.

13. The method of claim 9 further comprising providing one or more alerts and/or suggestions for diagnoses and immediate treatment guidelines.

14. The method of claim 13 further comprising providing the medical staff including a neurosurgeon, neurologist, specialist with the one or more alerts and/or suggestions by data stream.

15. The method of claim 13 further comprising providing the one or more alerts and/or suggestions to the medical staff including the neurosurgeon, neurologist, specialist onsite or at a remote location.

16. The method of claim 9 wherein the AI-based diagnostic guidance is for a patient presenting with neurological indications including but not limited to one or more of cerebral edema, raised intracranial pressure (ICP), ischemic stroke/hypo density recognition, ventricle size anomalies, indications of skull fracture, decompensating tumors, hemorrhagic and large ischemic stroke, and post-operative decompensation.

17. At least one non-transitory computer readable medium that includes program codes for providing artificial intelligence (AI)-based diagnostic guidance for a patient, the program codes comprising instructions causing one or more processors to perform operations comprising:
scanning a body portion of the patient and capturing, by using one or more radiology scanners, radiological scan images of the body portion of the patient;
receiving the captured radiological scan images of the patient;
receiving input data comprising one or more selected from the group consisting of (i) natural language input data received from an Emergency Room (ER) terminal or an ER device of medical personnel, (ii) real-time vital signs telemetry data of the patient received from a patient monitoring and data-logging computer, (iii) clinical laboratory testing results data of the patient received from at least one clinical laboratory data-logging computer, and (iv) patient historical data of the patient received from one or more medical record server;
recognizing patterns of the received radiological scan images of the patient to detect abnormality;
reconstructing the received radiological scan images of the patient into three-dimensional reconstructed scans;
generating patient imaging information based on the recognized patterns of the received radiological scan images of the patient and the three-dimensional reconstructed scans;
identifying problems, based on predetermined AI criteria and deep-learning based on patient-specific patterns and responses, by using one or more selected from the group consisting of natural language key words and phrases, logic, comparisons with prior related problems, databases of known problems with solutions, the patient imaging information, and the input data;
prioritizing the problems to a hot list based on what is important to rule-out and what is most likely based on the patient imaging information and the input data; and
providing medical staff with AI-generated interim diagnostic alerts and/or guidance based on the identified and prioritized problems.

18. The at least one non-transitory computer readable medium of claim 17 wherein the operations further comprise receiving one or more selected from the group consisting of (i) neurosurgical treatment database information and (ii) neurosurgical treatment guideline information from one or more neurosurgical database and treatment guideline servers that include the national treatment guidelines.

19. The at least one non-transitory computer readable medium of claim 18 wherein the instructions cause the one or more processors to provide the interim medical advice and the diagnostic guidelines based on the national treatment guidelines.

20. The at least one non-transitory computer readable medium of claim 17 wherein the operations further comprise providing one or more alerts and/or suggestions for diagnoses and immediate treatment guidelines.

21. The at least one non-transitory computer readable medium of claim 17 wherein the AI-based diagnostic guidance is for a patient presenting with neurological indications including but not limited to one or more of cerebral edema, raised intracranial pressure (ICP), ischemic stroke/hypo density recognition, ventricle size anomalies, indications of skull fracture, decompensating tumors, hemorrhagic and large ischemic stroke, and post-operative decompensation.

22. The system of claim 1 wherein imaging post-processor is integrated into the AI hub.

23. The system of claim 1 wherein the real-time vital signs telemetry data comprise one or more selected from the group consisting of blood pressure (BP), heart rate (HR), respiratory rate RR), temperature, electrocardiogram (EKG), electroencephalogram (EEG), electroencephalogram (EEG) and oximetry, and the clinical laboratory testing results data comprise one or more selected from the group consisting of hematology data, microbiology data, chemistry data, toxicology data and pathology data.

24. The method of claim 17 wherein the real-time vital signs telemetry data comprise one or more selected from the group consisting of blood pressure (BP), heart rate (HR), respiratory rate (RR), electrocardiogram temperature, (EKG), electroencephalogram (EEG), electroencephalogram (EEG) and oximetry, and the clinical laboratory testing results data comprise one or more selected from the group consisting of hematology data, microbiology data, chemistry data, toxicology data and pathology data.

* * * * *